(12) United States Patent
Bogdanović et al.

(10) Patent No.: US 6,303,093 B1
(45) Date of Patent: Oct. 16, 2001

(54) METHOD FOR MANUFACTURING TRANSITION-METAL CARBIDES, AND THEIR USE AS CATALYSTS

(75) Inventors: Borislav Bogdanović; Manfred Schwickardi, both of Mülheim an der Ruhr (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/214,531

(22) PCT Filed: Jul. 3, 1997

(86) PCT No.: PCT/EP97/03515

§ 371 Date: Jan. 6, 1999

§ 102(e) Date: Jan. 6, 1999

(87) PCT Pub. No.: WO98/02383

PCT Pub. Date: Jan. 22, 1998

(30) Foreign Application Priority Data

Jul. 12, 1996 (DE) ................................................ 196 28 160

(51) Int. Cl.$^7$ ...................................................... C01B 31/30
(52) U.S. Cl. ............................................. 423/439; 423/440
(58) Field of Search ...................................... 423/439, 440

(56) References Cited

U.S. PATENT DOCUMENTS 4,789,534 * 12/1988 Laine ................................... 423/439
4,812,301 * 3/1989 Davidson et al. ................... 423/440
5,338,523 * 8/1994 Kristic ................................. 423/439

FOREIGN PATENT DOCUMENTS

2747016 * 4/1978 (DE) .
9528352 * 10/1995 (WO) .

* cited by examiner

Primary Examiner—Stuart L. Hendrickson
(74) Attorney, Agent, or Firm—Norris McLaughlin & Marcus

(57) ABSTRACT

The present invention relates to a process for the preparation of transition metal carbides from transition metal/magnesium chlorides and perchlorinated organic compounds.

6 Claims, 3 Drawing Sheets

Figure 1:
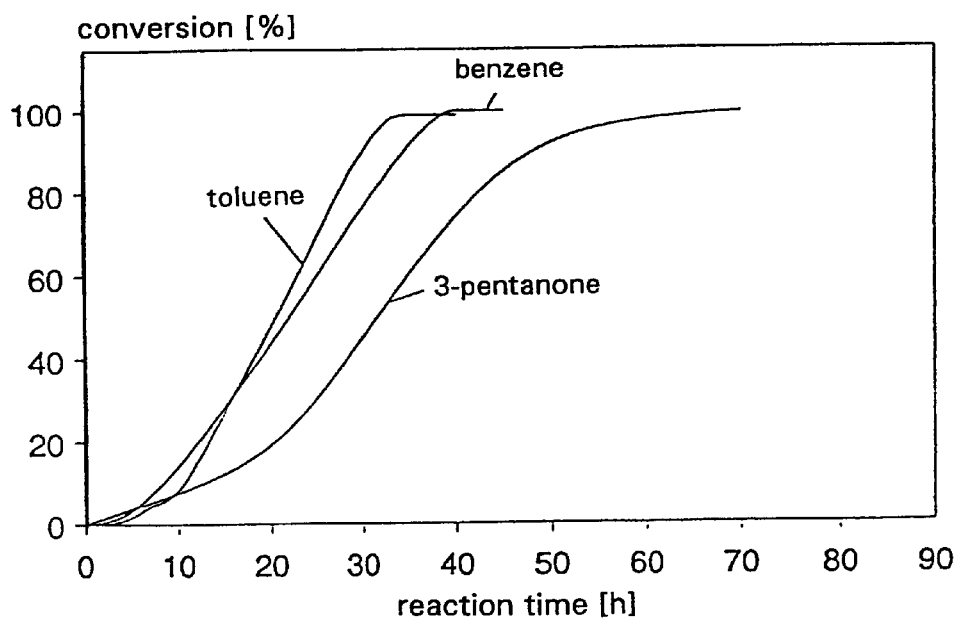

Hydrogenation of pyridine at 91 °C under pressure

Hydrogenation of toluene at room temperature under pressure

Hydrogenation of phenol at 90 °C under pressure

Hydrogenation of thymol at 90 °C under pressure

METHOD FOR MANUFACTURING TRANSITION-METAL CARBIDES, AND THEIR USE AS CATALYSTS

This application is a 371 of PCT/EP97/03515, which was filed on Jul. 3, 1997.

The present invention relates to a process for the preparation of novel or known transition metal carbon compounds (transition metal carbides) and their use as catalysts.

According to U.S. Pat. No. 5,385,716 (1995) and the European Patent Application 0 469 463 (1991), soluble transition metal/magnesium chloride complexes of general formula [M(MgCl)$_m$(MgCl$_2$)$_n$], M=transition metal, m=1, 2, 3, n=0–1, the so-called "inorganic Grignard reagents", can be prepared by the reaction of transition metal chlorides with magnesium or organomagnesium compounds in, e.g., tetrahydrofuran (THF).

Surprisingly, it has now been found that the inorganic Grignard reagents react with perchloroalkanes or -alkenes and with perchloroaromatics in, e.g., THF with elimination of the organic chlorine in the form of MgCl$_2$ and with the simultaneous formation of transition metal carbides of metals of groups 4 to 10 of the Periodic Table. Preferred are metals of groups 4 and 10, of which titanium, ruthenium, iridium and rhodium are more preferred. This finding has been surprising because the mentioned organic chlorine compounds are considered rather inert towards nucleophilic reactants, such as metals or organometallic compounds. The thus prepared, novel or known metal carbides are found to be effective as highly active heterogeneous hydrogenation catalysts. In the following, the invention will be further illustrated by way of some examples.

The Grignard reagents of ruthenium and iridium, [Ru(MgCl)$_3$] and [Ir(MgCl)$_3$], which can be prepared according to the cited literature, react with tetrachloroethene in a molar ratio of, e.g., 4:3 with elimination of MgCl$_2$ to form as yet unknown ruthenium and iridium carbides of empirical composition Ru$_4$C$_6$(MgCl$_2$)$_p$(THF)$_q$ (1) and Ir$_4$C$_6$(MgCl$_2$)$_p$(THF)$_q$ (2), respectively.

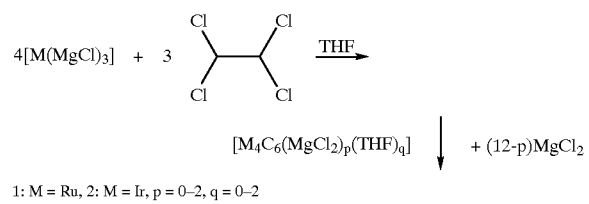

1: M = Ru, 2: M = Ir, p = 0–2, q = 0–2

The black, diamagnetic solids 1 and 2, which are insoluble in diluted acids, are X-amorphous; after annealing (600° C.), reflections from Ru or Ir metal appear in the X-ray powder diagram. An examination of 1 and 2 by means of matrix-supported laser desorption/ionization mass spectrometry (MALDI; C. A. Mitchell et al., Angew. Chem. 1996, 108, 1076) yielded mass peaks which, among others, corresponded to Ru$_x$C$_y$, x=1–8, y=3–8, and Ir$_x$C$_y$, x=1–3, y=2, 3 (measurements made by Ch. Yeretzian, Inst. für Physikal. und Theoret. Chemie der TU München, 1995).

Solid 1 was also examined by means of the extended X-ray absorption fine structure (EXAFS) method, which yielded the following result:

TABLE 1

| back-scattering atom | distance of back-scattering atom [Å] | coordination number |
|---|---|---|
| Ru | 2.64 | 2–3 |
| C | 2.08 | 2 |

According to the results obtained from the EXAFS spectrum, 1 consists of extremely small Ru clusters (3–4 Ru atoms) which are bonded to carbon atoms via direct bonds.

Figure 2:
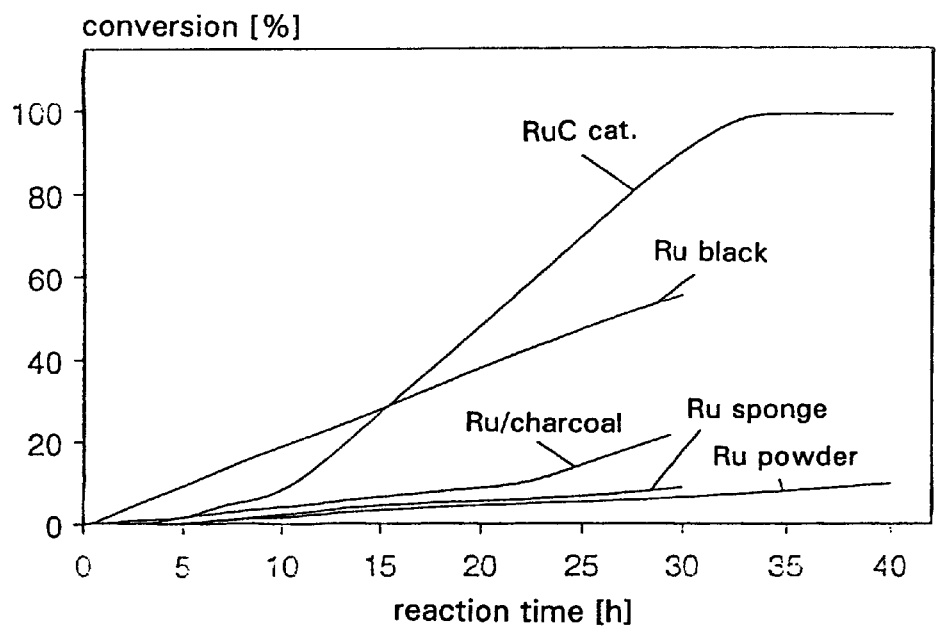
Figure 3:
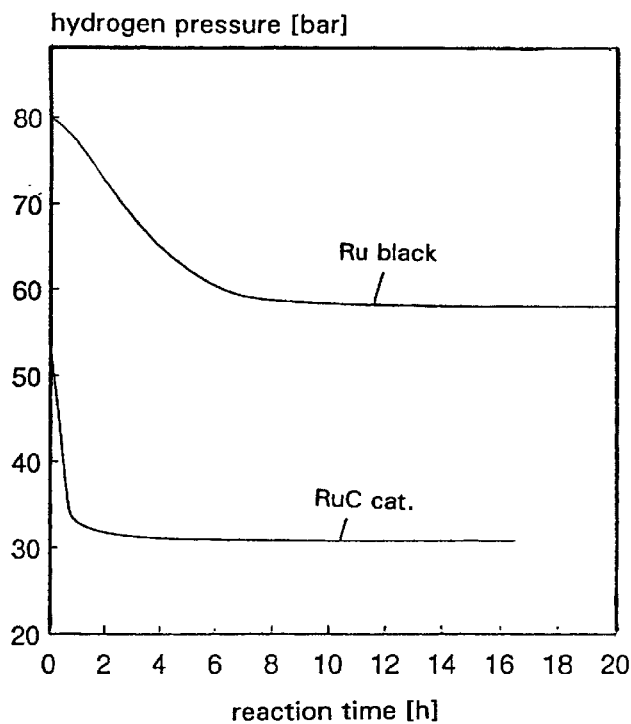
Figure 4:
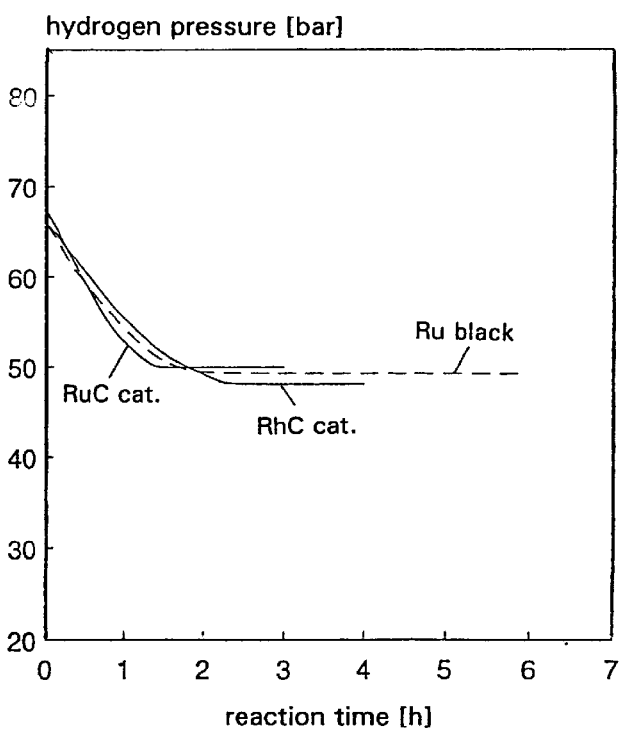

The Ru carbide 1, which can be isolated, proves to be a highly reactive heterogeneous catalyst for the hydrogenation of substrates considered difficult to hydrogenate, such as benzene, toluene and 3-pentanone, which can be hydrogenated quantitatively using 1 as a catalyst at room temperature (RT) and normal pressure to give cyclohexane, methylcyclohexane and 3-pentanol, respectively (FIG. 1). When toluene is hydrogenated under these conditions, the catalyst shows a higher catalytic activity than that of the commercial Ru catalysts used for comparison (FIG. 2). A catalytic activity which is higher than that of Ru black by some orders of magnitude is found using 1 as a catalyst in the hydrogenation of pyridine to piperidine (99.7%) under pressure (FIG. 3; cf. Tetrahedron: Asymmetry 1996, 71, 313). Under H$_2$ pressure, a rapid hydrogenation of toluene to give methylcyclohexane is also possible using 1 as a catalyst (FIG. 4). Using 1 as a catalyst, phenol can also be hydrogenated to cyclohexanol. Thymol is hydrogenated to the four stereoisomers of menthol using 1 as a catalyst.

Further examples of transition metal carbides prepared from inorganic Grignard reagents and perchloroorganic compounds include Ru carbides from Ru(MgCl)$_3$ and carbon tetrachloride or hexachlorobenzene, and Ti carbides from [Ti(MgCl)$_2$] (J. Organometal. Chem. 1993, 459, 87) and tetrachloroethene or carbon tetrachloride. The EXAFS spectrum of the titanium carbide obtainable from [Ti(MgCl)$_2$] and tetrachloroethene exhibits a carbon deficiency (TiCl$_{1-x}$) and in addition contains another unknown Ti-C component richer in carbon.

To date, metal carbides have been prepared by any of the following methods: 1. by combining the metals or metal oxides with carbon at temperatures above 1000° C.; 2. from metals or metal compounds and a gaseous carbonaceous compound (CO, CH$_4$); 3. from gaseous precursors by vapor deposition for preparing carbide thin films; 4. reduction of metal halides with LiBEt$_3$H in an organic solvent, e.g., THF.

The technical progress of the present process is that novel transition metal carbides as well as the previously known ones can be produced on a new synthetic route under extremely mild reaction conditions and with beneficial application properties (high catalytic activity, finely divided condition).

The experiments described in the following were performed in an argon atmosphere. The solvents used were deaerated and anhydrous.

EXAMPLE 1

To a solution of 10.2 mmol of [Ru(MgCl)$_3$] (prepared according to Chem. Mater. 1995, 7, 1153; Mg$^{2+}$ content: 31.8 mmol, Cl$^-$ content: 31.0 mmol) in 50 ml of THF was added a solution of 0.73 ml (7.14 mmol) of tetrachloroethene in 10 ml of THF dropwise with stirring in the course of one hour; the reaction mixture temporarily warmed up to 40° C. The mixture was stirred at room temperature for another 4 h and then refluxed for 16 h. After diluting with 20 ml of THF, the black suspension was filtered over a D4 glass frit, the solid was washed three times with THF and then dried under high vacuum at 100° C. for 3 h to obtain 1.44 g of Ru carbide 1 as a black amorphous powder. Elemental analysis: Ru 62.59%, C 21.27%, H 2.23%, Mg 5.07%, Cl 5.94%.

Compound 1 thus obtained was employed as a hydrogenation catalyst (RuC cat.; Examples 3–9). The Cl$^-$ content of the filtrate was 57 mmol (by the Volhard method). The increase of Cl$^-$ ions in solution (26 mmol) corresponds to a tetrachloroethene conversion of 91%. The remaining chlorine (2.4 mmol) is found in 1 as seen from the elemental analysis, and thus the Cl balance is 99.7%.

EXAMPLE 2

The preparation and isolation of the Ir carbide 2 was performed by analogy with that of Ru carbide 1. Starting materials: 22.5 ml of an [Ir(MgCl)$_3$] solution in THF with 3.33 mmol of Ir, 10.4 ml of Mg$^{2+}$, 10.4 mmol of Cl$^-$, and a solution of 0.21 ml (2.06 mmol) of tetrachloroethene in 2 ml of THF; duration of dropwise addition: 0.5 h; peak of temperature: 50° C. Duration of subsequent reaction at room temperature: 18 h. Yield of Ir carbide 2 as a black amorphous powder: 0.78 g. Elemental analysis: Ir 72.18%, C 13.46%, H 1.52%, Mg 3.96%, Cl 4.08%. The Cl$^-$ content of the filtrate was 18.6 mmol; the increase of Cl$^-$ ions in solution (8.2 mmol) corresponds to a tetrachloroethene conversion of 99.5%.

EXAMPLE 3 (Application Example)

To 1.1 ml (12.3 mmol) of benzene was added 23.6 mg (1.5% by weight) of Ru carbide catalyst 1 (RuC cat.; Example 1). At room temperature and normal pressure, the suspension was put under hydrogen gas which could be replenished from an automatically recording gas burette, and hydrogen absorption began as the suspension was intensely stirred. Until the hydrogenation was completed under these conditions (see FIG. 1), 862 ml of H$_2$ (21° C., normal pressure, 97% of theory) was consumed. The hydrogenation product which was separated from the catalyst by filtration consisted of 99.97% cyclohexane according to GC analysis.

EXAMPLE 4 (Application Example)

The hydrogenation of 1.3 ml (12.2 mmol) of toluene in the presence of 24.2 mg of the RuC catalyst (1.5% by weight Ru) was performed by analogy with Example 3. Hydrogen uptake: 880 ml of H$_2$ at 20° C., normal pressure (see FIGS. 1 and 2; 99% of theory). Hydrogenation product: 99% methylcyclohexane. As can be seen from FIG. 2, the RuC catalyst exhibits a higher catalytic activity than that of Ru black, Ru sponge, Ru powder or Ru on charcoal under the hydrogenation conditions employed.

EXAMPLE 5 (Application Example)

The hydrogenation of 1.0 ml (9.5 mmol) of 3-pentanone in the presence of 23.3 mg of the RuC catalyst (1.8% by weight Ru) was performed by analogy with Example 3. Hydrogen uptake: 225 ml of H$_2$ at 21° C., normal pressure (see FIG. 1; 99% of theory). Hydrogenation product: 99.6% 3-pentanol.

EXAMPLE 6 (Application Example)

The hydrogenation of 5.0 ml (61.8 mmol) of absolute pyridine in the presence of 39.3 mg of the RuC catalyst (0.5% by weight Ru) was performed in an autoclave equipped with a magnetic stirring bar at 91° C. (inside temperature) and an initial hydrogen pressure of 54 bar. The course of the hydrogenation reaction in comparison with the corresponding hydrogenation of pyridine with Ru black as the catalyst is shown in FIG. 3. Since the RuC catalyst seemingly dissolved during the hydrogenation, the hydrogenation product was separated from the catalyst by distillation in vacuo (0.1 mbar). Hydrogenation product: 5.10 g (97% of theory) of piperidine of 99.7% purity.

EXAMPLE 7 (Application Example)

The hydrogenation of 5.0 ml (47 mmol) of toluene in the presence of 36.2 mg of the RuC catalyst (0.5% by weight Ru) was performed by analogy with Example 6 under an H$_2$ pressure of 54 bar (initial pressure) at room temperature. The course of the H$_2$ uptake is shown in FIG. 4. The hydrogenation product which was separated from the catalyst by filtration (4.53 g) consisted of 99.3% methylcyclohexane according to GC analysis.

EXAMPLE 8 (Application Example)

Figure 5:
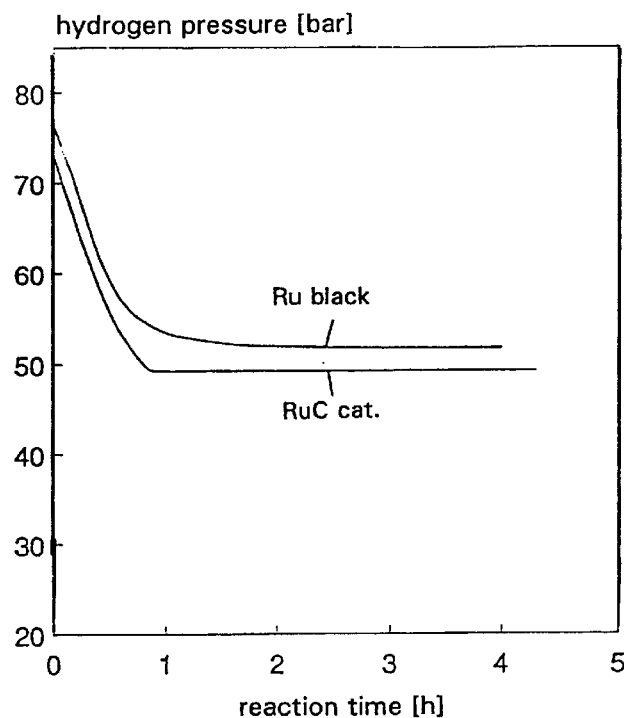

The hydrogenation of 5.01 g (53.2 mmol) of phenol in 10 ml of THF in the presence of 42 mg of the RuC catalyst (0.5% by weight Ru) was performed by analogy with Example 6 under an initial H$_2$ pressure of 73 bar at 90° C. The course of the H$_2$ uptake is shown in FIG. 5. The hydrogenation product which was separated from the catalyst by filtration (13.1 g) contained 39.4% of cyclohexanol (the rest being THF) and no other components as seen from the GC.

EXAMPLE 9 (Application Example)

Figure 6:
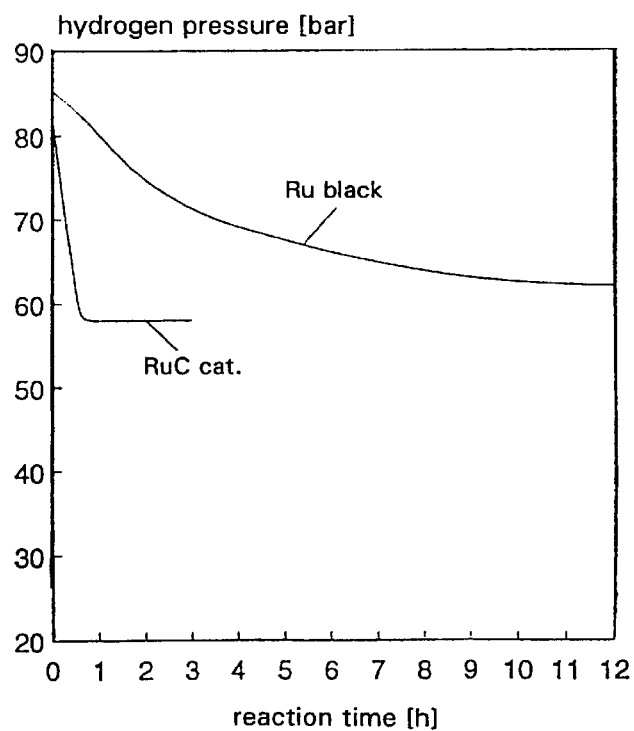

The hydrogenation of 9.74 g (64.8 mmol) of thymol in 10 ml of THF in the presence of 81 mg of the RuC catalyst (0.5% by weight Ru) was performed by analogy with Example 6 under an initial H$_2$ pressure of 81 bar at 90° C. The course of the H$_2$ uptake is shown in FIG. 6. The hydrogenation product which was separated from the catalyst by filtration (17.3 g) consisted of 55.8% (the rest being THF) of the four stereoisomer's of menthol only. Distribution of isomers: neomenthol 10.0%, neoisomenthol 50.2%, menthol 6.4%, isomenthol 33.4%.

EXAMPLE 10 (Application Example)

The hydrogenation of 9.70 g (64.6 mmol) of thymol in 10 ml of THF in the presence of 68.5 mg of the IrC catalyst (Example 2, 0.5% by weight Ir) was performed by analogy with Example 6 under an initial H$_2$ pressure of 80 bar at 90° C. The hydrogenation product which was separated from the catalyst by filtration consisted of (besides THF) 16.3% of thymol and 83.7% of the four stereoisomers of menthol. Distribution of isomers: neomenthol 23.4%, neoisomenthol 68.4%, menthol 5.5%, isomenthol 2.7%.

EXAMPLE 11

The preparation of a Ru carbide from [Ru(MgCl)$_3$] and CCl$_4$ was performed by analogy with that of Ru carbide 1. Starting materials: 20.0 ml of an [Ru(MgCl)$_3$] solution in THF with 3.8 mmol of Ru and 11.9 mmol of Cl$^-$, and a solution of 0.24 ml (2.49 mmol) of CCl$_4$ in 4 ml of THF. Duration of dropwise addition: 0.5 h; peak of temperature: 45° C. Duration of subsequent reaction: 3 h at room temperature and 8 h at reflux temperature. Yield of the Ru carbide: 0.46 g (Ru 69.16%, C 17.53%, H 2.04%, Mg 3.36%, Cl 9.83%, corresponding to Ru$_4$C$_3$(MgCl$_2$)$_{0.8}$(THF)$_{1.4}$). The Cl$^-$ content of the filtrate was 20.3 mmol; the increase of Cl⁻ ions in solution (8.4 mmol) corresponds to a carbon tetrachloride conversion of 84%.

EXAMPLE 12

The preparation of a Ru carbide from [Ru(MgCl)$_3$] and hexachlorobenzene was performed by analogy with that of Ru carbide 1. Starting materials: 20.0 ml of an [Ru(MgCl)$_3$] solution in THF with 3.8 mmol of Ru and 11.9 mmol of Cl⁻, and a suspension of 0.48 g (1.68 mmol) of C$_6$Cl$_6$ in 6 ml of THF. Duration of dropwise addition: 0.5 h; peak of temperature: 35° C. Duration of subsequent reaction: as in Example 11. Yield of the Ru carbide: 0.49 g (Ru 64.78%, C 19.01%, H 2.35%, Mg 3.56%, Cl 11.69%). The Cl⁻ content of the filtrate was 19.8 mmol; the increase of Cl⁻ ions in solution (7.9 mmol) corresponds to a C$_6$Cl$_6$ conversion of 78%.

EXAMPLE 13

The preparation of a Ti carbide from [Ti(MgCl)$_2$.0.5 MgCl$_2$] (J. Organometal. Chem. 1993, 459, 87) and tetrachloroethene was performed by analogy with that of Ru carbide 1. Starting materials: 200 ml of a [Ti(MgCl)$_2$.0.5 MgCl$_2$] solution in THF with 18.7 mmol of Ti and 58.4 mmol of Cl⁻, and 0.84 ml (8.22 mmol) of tetrachloroethene. Duration of dropwise addition: 0.5 h; peak of temperature: 40° C. Duration of subsequent reaction: 2 h at room temperature and 17 h at reflux temperature. Yield of the Ti carbide: 2.02 g (Ti 42.75%, C 21.42%, H 2.34%, Mg 4.75%, Cl 18.95%, corresponding to TiCMg$_{0.2}$Cl$_{0.6}$(THF)$_{0.25}$) The Cl⁻ content of the filtrate was 88.2 mmol; the increase of Cl⁻ ions in solution (29.8 mmol) corresponds to a tetrachloroethene conversion of 91%.

EXAMPLE 14

The preparation of a Ti carbide from [Ti(MgCl)$_2$.0.5 MgCl$_2$] (see Example 13) and CCl$_4$ was performed by analogy with that of Ru carbide 1. Starting materials: 120 ml of a [Ti(MgCl)$_2$.0.5 MgCl$_2$] solution in THF with 11.2 mmol of Ti and 35.0 mmol of Cl⁻, and 0.50 ml (5.2 mmol) of CCl$_4$. Duration of dropwise addition: 0.5 h; peak of temperature: 42° C. Duration of subsequent reaction: see Example 13. Yield of the Ti carbide: 0.9 g (Ti 43.34%, C 19.01%, H 4.05%, Mg 4.70%, Cl 16.58%, corresponding to Ti$_2$CMg$_{0.4}$Cl$_{1.0}$(THF)$_{ca.0.6}$) The Cl⁻ content of the filtrate was 50.0 mmol; the increase of Cl⁻ ions in solution (15 mmol) corresponds to a CCl$_4$ conversion of 72%.

EXAMPLE 15

The preparation and isolation of a Rh carbide was performed by analogy with that of Ru carbide 1 in Example 1. Starting materials: 30 ml of an [RhMgCl.MgCl$_2$] solution in THF with 2.94 mmol of Rh and 8.82 mmol of Cl⁻, and 0.067 ml (0.66 mmol) of tetrachloroethene. Duration of reaction: 24 h at room temperature. Yield of the Rh carbide as a black amorphous powder: 0.39 g. The Cl⁻ content of the filtrate was 10.9 mmol; the increase of Cl⁻ ions in solution (2.13 mmol) corresponds to a tetrachloroethene conversion of 81%.

EXAMPLE 16 (Application Example)

The hydrogenation of 5.0 ml (47 mmol) of toluene in the presence of 33.7 mg of the RhC catalyst (Example 15; 0.5% by weight Rh) was performed by analogy with Example 6 under an initial H$_2$ pressure of 54 bar at room temperature (FIG. 4). The hydrogenation product which was separated from the catalyst by filtration (4.47 g) consisted of 100% methylcyclohexane.

What is claimed is:

1. A process for preparing a product consisting of transition metal atoms and carbon atoms, said process comprising reacting a soluble complex M(MgCl)$_m$(MgCl$_2$)$_n$, wherein M represents a transition metal of groups 4 to 10 of the Periodic Table, m=1, 2 or 3, and n=0–1, with a perchloroorganic compound.

2. The process according to claim 1, wherein the perchloroorganic compound is selected from the group consisting of tetrachloroethene, carbon tetrachloride and hexachlorobenzene.

3. The process according to claim 1, wherein said reacting is performed in an ether solvent.

4. The process according to claim 3, wherein said ether solvent is tetrahydrofuran.

5. The process according to claim 1, wherein said reacting is performed at a temperature ranging from 0° C. to a boiling temperature of a solvent employed.

6. The process according to any one of claims 1–5, which further comprises preparing said soluble complex M(MgCl)$_m$(MgCl$_2$)$_n$ by reacting a transition metal chloride and magnesium or an organomagnesium compound in an ether solvent.

* * * * *